(12) United States Patent
Shang et al.

(10) Patent No.: US 10,622,780 B2
(45) Date of Patent: Apr. 14, 2020

(54) HANDPIECE WITH A MICROCHIP LASER

(71) Applicant: Candela Corporation, Wayland, MA (US)

(72) Inventors: Xiaoming Shang, Lexington, MA (US); Christopher J. Jones, Leicester, MA (US); Zhi Huang, Boston, MA (US)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 16/015,249

(22) Filed: Jun. 22, 2018

(65) Prior Publication Data
US 2019/0393668 A1 Dec. 26, 2019

(51) Int. Cl.
| | |
|---|---|
| H01S 3/10 | (2006.01) |
| H01S 3/094 | (2006.01) |
| H01S 3/11 | (2006.01) |
| H01S 3/091 | (2006.01) |
| H01S 3/06 | (2006.01) |
| H01S 3/00 | (2006.01) |
| H01S 3/16 | (2006.01) |
| A61N 5/06 | (2006.01) |
| A61N 5/067 | (2006.01) |

(52) U.S. Cl.
CPC ...... *H01S 3/094084* (2013.01); *A61N 5/0616* (2013.01); *H01S 3/0071* (2013.01); *H01S 3/0621* (2013.01); *H01S 3/0625* (2013.01); *H01S 3/0627* (2013.01); *H01S 3/091* (2013.01); *H01S 3/1115* (2013.01); *H01S 3/1611* (2013.01); *H01S 3/1623* (2013.01); *H01S 3/1633* (2013.01); *H01S 3/1643* (2013.01); *A61N 2005/063* (2013.01); *A61N 2005/067* (2013.01); *A61N 2005/0644* (2013.01); *H01S 3/0092* (2013.01); *H01S 3/1685* (2013.01)

(58) Field of Classification Search
CPC ............. H01S 3/094084; H01S 3/0071; H01S 3/0621; H01S 3/1115; H01S 3/1611; H01S 3/1643; H01S 3/1685; H01S 3/1623; H01S 3/0092; H01S 3/0627; H01S 3/0625
See application file for complete search history.

(56) References Cited

U.S. PATENT DOCUMENTS

| | | | | |
|---|---|---|---|---|
| 5,394,413 A | * | 2/1995 | Zayhowski | ............ G01N 21/63 372/10 |
| 9,810,775 B1 | * | 11/2017 | Welford | ................ G01S 7/4814 |

(Continued)

OTHER PUBLICATIONS

International Search Report and Written Opinion in PCT/US2019/037418 dated Dec. 2, 2019.

(Continued)

*Primary Examiner* — Kinam Park
(74) *Attorney, Agent, or Firm* — Manelli Selter PLLC; Edward Stemberger

(57) ABSTRACT

A microchip laser and a handpiece including the microchip laser. The microchip laser includes a laser medium with input and output facets. The input facet is coated with a highly reflective dielectric coating at microchip laser wavelength and highly transmissive at pump wavelength. The output facet is coated with a partially reflective at microchip laser wavelength dielectric coating. A saturable absorber attached by intermolecular forces to output facet of microchip laser. A handpiece for skin treatment includes the microchip laser.

16 Claims, 7 Drawing Sheets

(56) References Cited

U.S. PATENT DOCUMENTS

| 9,843,157 B2* | 12/2017 | Williams | H01S 3/1698 |
| 2008/0082089 A1* | 4/2008 | Jones | A61B 18/203 |
| | | | 606/9 |
| 2016/0294152 A1* | 10/2016 | Bhawalkar | H01S 3/1611 |
| 2017/0133815 A1* | 5/2017 | Kopf | H01S 3/0627 |
| 2017/0358898 A1* | 12/2017 | Taira | H01S 3/0405 |

OTHER PUBLICATIONS

Butler et al., "Scanling Q-switched microchip lasers for shortest pulses", Applied Physics B, Lasers and Optics, Springer, Berlin, DE, vol. 109, No. 1 pp. 81-88, Sep. 22, 2012.
International Search Report and Provisional Opinion in PCT/US2019/037418 dated Jun. 17, 2019.

* cited by examiner

# HANDPIECE WITH A MICROCHIP LASER

TECHNOLOGY FIELD

The present system relates to a passively Q-switched microchip laser packaged in a handpiece and in particular to microchip lasers with double pass pumping configuration.

BACKGROUND

Systems for non-invasive treatment of skin disorders known in the art. Typically, such system includes a cabinet into which a laser is placed and an articulated arm connected a handpiece that conducts the laser radiation from the laser to a segment of skin to be treated. The functionality of such a system is limited by the capabilities of the selected laser. Treatment of skin imperfections usually requires more than one type of laser and frequently more than one type of laser is placed in the cabinet. This increases size, cost and complexity of the system.

Treatment of some skin imperfections requires significant laser power (tens and even hundreds of MW) that in order to prevent skin damage is supplied in ultrashort femto or picosecond pulses. Such laser power is difficult to transfer through a fiber and use of articulated arm significantly limits the freedom of the caregiver.

Microchip lasers are alignment-free monolithic solid-state lasers where the active laser media is in direct contact with the end mirrors forming the laser resonator. In many cases the mirrors, which are dielectric coatings, are simply deposited on the end faces of the active laser media. Microchip lasers are usually pumped with a laser diode and typically emit on average a few tens or hundreds milliwatts of power, although reports of microchip lasers emitting 10 W have been published. The dimensions of the microchip laser are small and support their placement in almost any desired place in the system.

A typical Q-switched microchip lasers consist of a laser medium and a saturable absorber as a passive Q-switcher bonded together as one element. Microchip lasers are small, linear cavity, monolithic solid-state lasers with dielectrically coated cavity mirrors. The typical cavity length is on the order of millimeter. The short cavity lengths result in extremely short cavity lifetimes, and the possibility of much shorter Q-switched pulses. It has been demonstrated that Q-switched microchip lasers can produce output pulses shorter than 300 ps, as short as large mode-locked lasers produce with peak powers of about 10 KW, similar to commercially available large Q-switched systems produce.

Over decades, a lot of effort has been put in places striving for generation of high energy picosecond lasers. Many techniques have been developed. These techniques commonly involve multi-stage configurations, i.e., a low energy picosecond seed laser, for example nJ or µJ are fed into amplification stages (including regenerative amplifier or/and multi-pass amplifications). Such multi-stage configurations require complex optical arrangement and sophisticated electronic synchronization further increasing the complexity and cost of the system.[16, 17, 18, 20, 25, 28]

SUMMARY

Disclosed is a microchip laser and a method to implement a handpiece with passively Q-switched microchip laser with double pass pumping geometry. The laser medium and saturable absorber are sandwiched with a highly reflective dielectric coating at pumping wavelength and bonded with optical contact by intermolecular forces. The highly reflective dielectric coating supports achieving double passing pumping and avoids unwanted bleaching of passive Q-switch by unabsorbed pump laser.

The dimensions of the microchip laser support the microchip laser packaging in a handpiece that can be used in different applications and in particular for skin disorders treatment. The handpiece is adapted to be applied to skin and slide over the skin. The handpiece could include a scanning system configured to scan a laser beam emitted by the microchip laser across a segment of skin. The scanning system could provide a one-dimensional (1-D) or a two-dimensional (2-D) treated skin area coverage. Fractionated micro-dot line beam pattern is supported. The microchip laser handpiece could contain second or higher order harmonic generator to generate an additional laser wavelength.

A system based on the microchip laser uses Alexandrite laser as a pump source. Alexandrite laser, which provides over 1 kW pumping power for higher pulse energy generation. The high pumping power facilitates energy storage that is further facilitated by use of a saturable absorber of low initial transmission. Generation of picosecond laser pulses with high peak power of about 100 MW and higher has been demonstrated.

LIST OF FIGURES AND THEIR BRIEF DESCRIPTION

For a more complete understanding of this disclosure and its features, reference is now made to the following description, taken in conjunction with accompanying drawings, in which like reference numerals denote like elements:

DESCRIPTION

Figure 1:
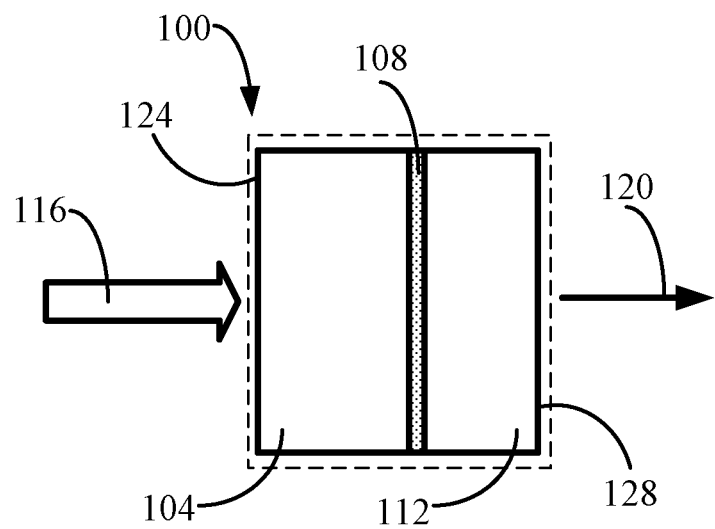
FIG. 1 is an example of a microchip laser.

The present disclosure suggest mounting of a passively Q-switched microchip laser in a handpiece, thereby reducing the size and complexity of the total system and improving the power utilization efficiency. The disclosure also suggests a novel and more robust microchip laser. The Q-switched microchip laser emits picosecond pulses at a laser power of tens and hundreds of MW.

The passively Q-switched microchip laser does not require switching electronics, thereby reducing the size and complexity of the total system and improving the power efficiency. In addition, there is no need for interferometric control of the cavity dimensions, simplifying production of the device and greatly relaxing the tolerances on temperature control during its use. The result is a potentially less expensive, smaller, more robust, and more reliable Q-switched laser system with performance comparable with that of the coupled cavity Q-switched microchip laser. With this combination of attributes, passively Q-switched picosecond microchip lasers are attractive for a large range of applications, including high-precision ranging, robotic vision, automated production, nonlinear frequency generation, environmental monitoring, micromachining, cosmetics and microsurgery, and ionization spectroscopy as well as automobile engine ignition.

Microchip Laser

Passively Q-switched microchip lasers have been investigated extensively for several decades. However, the most studies reported generation of less than a few millijoule pulse energy and less than 10 MW peak power [1-15, 19, 21-26, 28, 29]. In particular, some of microchip lasers were only capable to produce nanosecond laser pulse duration [3, 4, 7, 13, 23, and 24]. Most recently, X. Guo et. al demonstrated the generation of 12 mJ from Yb:YAG/Cr:YAG microchip laser[1]. However, only ~3.7 MW peak power was achievable due to longer pulse duration (1.8 ns). Furthermore the laser had to be operated under cryogenic condition (i.e., 77 degrees K) which makes practical application problematic. To the best knowledge of the inventor, the generation of >100 MW sub-nanosecond laser pulses has not been reported directly from passively Q-switched microchip laser.

Single pass pumped microchip lasers have several limitations. In order to ensure the sufficient absorption of pumping energy in the laser material, the laser medium has to be sufficiently long, however longer laser medium will lead to longer emitted pulse duration. In addition, at some particular pump wavelengths, the unabsorbed pump laser can result in unwanted bleaching of saturable absorber causing failure of Q-switching operation. To overcome these above-mentioned issues, the present disclosure introduces a microchip laser with double pass pumping. Double pass pumping also facilitates use of the laser medium produced from crystals which are difficult to be doped (i.e., Nd:YAG) or have a weak absorption of laser medium at the available pump laser wavelength. The double pass pumping can be made possible by applying highly reflective dielectric coating in between the laser material and passive Q-switch while two materials are bonded together to form microchip laser. The double pass pumped microchip laser supports pump laser absorption and shorter medium length leading to shorter pulse duration as well as a more compact laser layout.

The present disclosure describes a microchip laser for producing sub-nanosecond laser pulse with high peak power exceeding 100 MW.

Microchip laser 100 is shown in FIG. 1. Microchip laser 100 includes a laser medium 104, such as for example, Nd:YAG and Nd: a highly reflective dielectric coating 108 for pumping laser wavelength sandwiched in between laser medium 104 and a saturable absorber 112. Also shown in FIG. 1 are Alexandrite laser pumping beam 116 and microchip laser 100 output beam 120. The Alexandrite laser output beam 120 could be, for example a beam with ~752 nm wavelength. Highly reflective dielectric coating 108 (highly reflecting at pump laser wavelength, 752 nm and highly transmitting Q-switched laser wavelength, 1064 nm)) supports achieving double passing pumping and avoids unwanted bleaching of passive Q-switch 112 by unabsorbed pump laser leaking through it.

An input end 124 of the microchip laser 100 (i.e., the surface of laser material 104) is coated with a highly reflective at microchip laser 100 wavelength e.g., 1064 nm dielectric coating and highly transmissive at pump wavelength. The output end of microchip laser 100 i.e., surface 128 of passive Q-switch 112 is deposited with dielectric coating partially reflective at the microchip laser 100 emitted laser wavelength. The coating of output facet of the microchip laser considers the refractive indices of laser medium and saturable absorber such that the coating functions as required when the monolithic material is formed.

These two ends (124 and 128) are arranged to be parallel and coated with dielectric coating, allowing laser oscillation occurs.

Diffusion bonding is commonly used to bond laser material and passive Q-switching element (i.e. saturable absorber) to form passively Q-switched microchip laser. This method is typically accomplished at an elevated pressure and temperature, approximately 50-70% of the absolute melting temperature of the placed in contact materials. Such fabrication process involving elevated temperature and makes it difficult to deposit any form of dielectric coating in between two elements (i.e., laser medium and passive Q-switcher), in particular, highly reflective coating at pump laser wavelength. Therefore, single pass pumping can be only applied.

Figure 2:
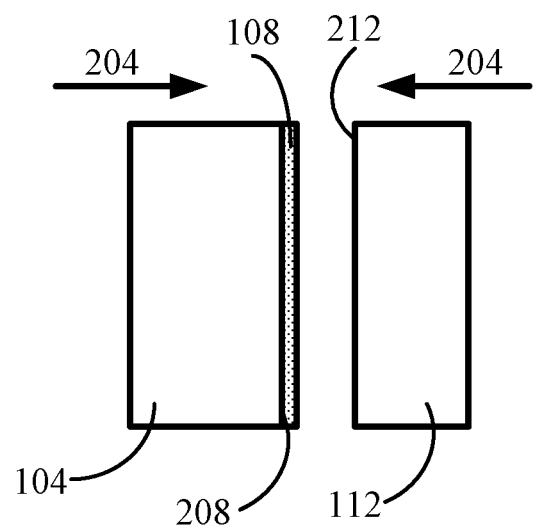
FIG. 2 is an example illustrating the bonding of laser medium and saturable absorber of a microchip laser.

In the current disclosure, the bonding between laser medium 104 and saturable absorber 112 is implemented as illustrated by arrows 204 through optical contact by intermolecular forces, such as Van der Waals forces, hydrogen bonds, and dipole-dipole interactions, as shown in FIG. 2. No elevated temperature and pressure is needed so that integrity of reflective dielectric coating 108 is protected.

The two surfaces of being contacted i.e., 208 of laser medium 104 and 212 of saturable absorber 112 are processed in optical quality to achieve stable optical contact. The highly reflective dielectric coating at an interface between laser medium 104 and saturable absorber 112 at pump wavelength supports achieving double passing pumping and avoids unwanted bleaching of passive Q-switch by unabsorbed pump laser. Generally, the surface quality could be better than 20-10 scratch-dig. The flatness and roughness could be at least $\lambda/4$ 10 A rms or better, respectively.

Microchip laser medium 100 and saturable absorber 112 could be Nd doped crystal (i.e., YAG or YLF or ceramic. The materials for the laser medium and saturable absorber can be of the same host material or of different materials. This is quite different from the existing microchip laser bonded through diffusion method where the material physical properties (i.e., melting point, thermal expansion coefficient, etc.) for two components should be similar.

The passively Q-switched microchip laser with double pass pumping offers advantage over that with single pass pumping by generating much shorter pulses due to the shorter laser material used. This is because of the Q-switched pulse duration is roughly proportional to the cavity length. Furthermore, for a crystal with low doping concentration or low absorption at pumping laser wavelength, double pass pumping makes it possible to obtain sufficient pump laser absorption while maintaining shorter crystal length leading to a more compact laser design.

The system uses Alexandrite laser as a pump source. Alexandrite laser which can provide over 1 kW pumping power for higher pulse energy generation. The high pumping power facilitates energy storage that is further facilitated by use of a saturable absorber of low initial transmission. Generation of picosecond laser pulses with high peak power of about 100 MW and higher has been demonstrated.

The high energy/high peak power ultrashort pulse microchip laser facilitates efficient non-linear frequency conversation including harmonic generation (second harmonic, third harmonic, fourth harmonic, sum frequency generation, OPO, etc) and super continuum generation where the high peak power is required. In contrast to the existing low energy microchip laser, the high energy microchip laser can provide higher energy/power at frequency converted wavelengths therefore significantly increase measurement precision by improving signal to noise ratio. Most importantly, the optical arrangement is very compact and simple and supports mounting of the microchip laser in constrained space for example, in a handpiece.

Figure 3:
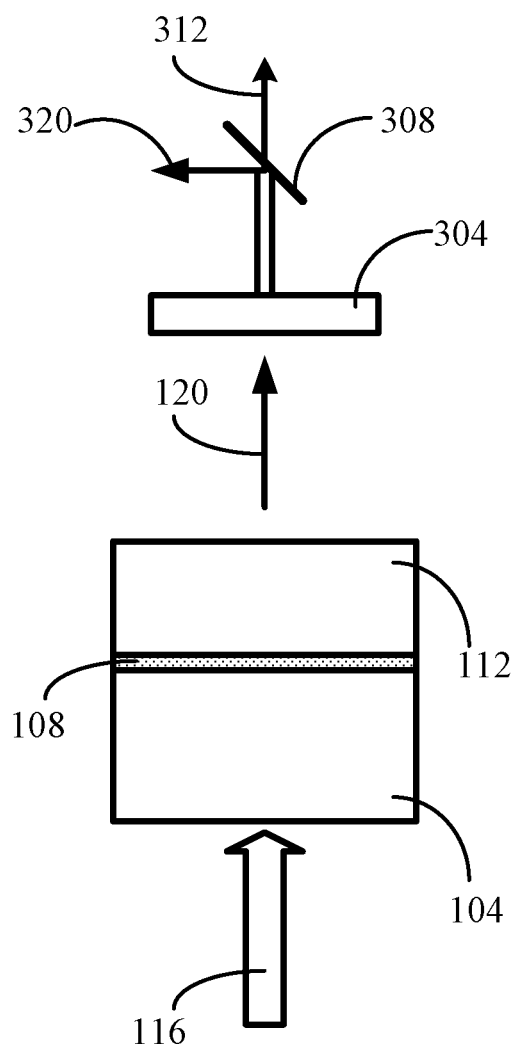
FIG. 3 is an example of a microchip laser supporting second harmonic generation (SHG)

FIG. 3 is an example of a microchip laser supporting second harmonic generation. For generation of stable linearly polarized Q-switched laser, <110> cut $Cr^{4+}$:YAG is used. A second harmonic generation crystal (SHG) 304, which could be such as lithium niobate ($LiNbO3$), potassium titanyl phosphate (KTP=$KTiOPO4$), and lithium triborate (LBO=$LiB3O5$) or any other SHG receives microchip laser 100 output beam 120 with wavelength of 1064 nm and transforms it into two beams—one beam 320 maintaining the original wavelengths (frequency) of 1064 nm and a beam 312 having a frequency two times higher than the original beam 120 has with a wavelength of 532 nm. Beam splitter 308 splits and directs in different directions beams 320 and 312 facilitating their use.

Figure 4:
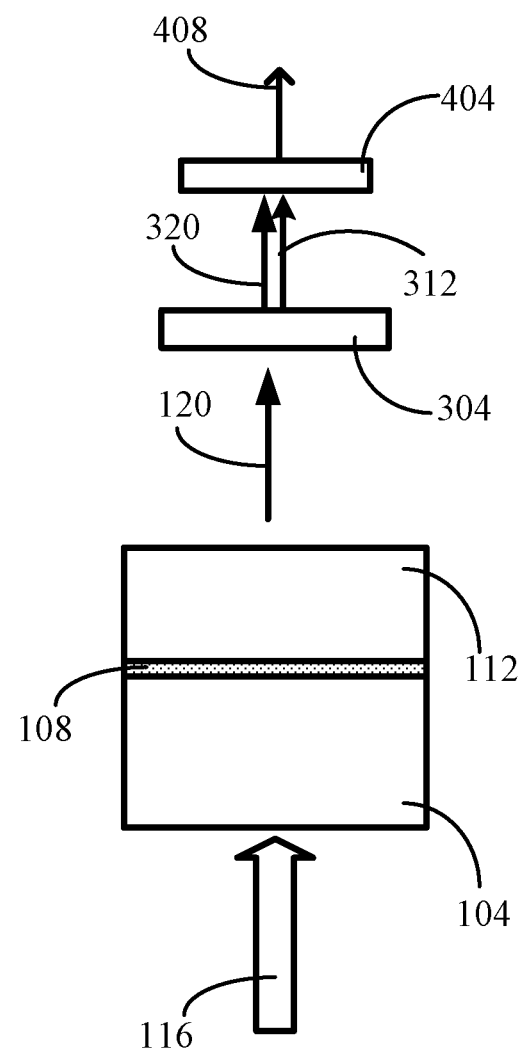
FIG. 4 is an example of a microchip laser supporting sum frequency generation (SFG)

FIG. 4 is an example of a microchip laser supporting sum frequency generation (SFG). Sum frequency generation (SFG) or difference frequency generation (DFG) can occur, where two laser pump beams generate another beam with the sum or difference of the optical frequencies of the pump beams 312 and 320 with wavelengths of 532 nm and 1064 nm. For example, mixing the output of a 1064-nm laser beam with frequency-doubled laser beam with 532 nm using a SFG crystal 404, would result in an output light beam 408 with 355-nm UV light.

Figure 5:
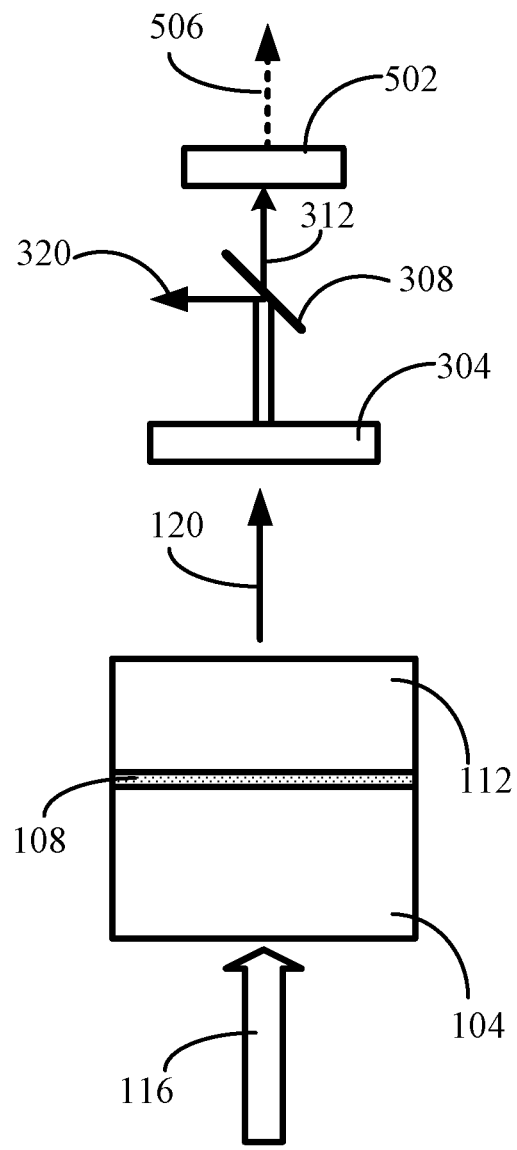
FIG. 5 is an example of a microchip laser supporting fifth harmonic generation (FHG)

FIG. 5 is an example of a microchip laser supporting fourth harmonic generation (FHG). The fourth harmonic generation is a process designed to produce UV-radiation for example at 266 nm or even shorter wavelengths. For example, the fourth harmonic of Nd:YAG laser producing a laser beam with wavelength of 1064 nm would be a light beam with wavelength of 266 nm. Numeral 502 marks an FHG crystal and numeral 506 marks an output beam with wavelength of 266 nm.

Such frequency conversation processes can offer a wide range of spectrum with sufficient energy for different spectroscopy application. In contrast to the existing low energy microchip lasers, this high energy microchip laser can provide higher energy/power at frequency converted wavelengths therefore significantly increase measurement precision by improving signal to noise ratio. The optical arrangement is very compact and simple.

The disclosed high peak power microchip laser producing picosecond pulses could be used in many additional to spectroscopy fields. These include skin treatment, micromachining, efficient non-linear frequency conversation including harmonic generation (second harmonic, third harmonic, fourth harmonic, sum frequency generation, OPO, etc) and super continuum generation where the high peak power is required. Such frequency conversation processes can offer a wide range of spectrum with energy for spectroscopy application.

Handpiece

One of potential and promising applications for the disclosed high peak power microchip laser producing picosecond laser pulses would be in cosmetic and medical laser systems. The high energy short pulse microchip laser supports packaging of the microchip laser into a handpiece to perform meaningful aesthetic treatment and in particular fractional skin rejuvenation. It has been demonstrated clinically that for laser pulses of a few hundred picosecond with 4 mJ per laser beam is sufficient enough to cause tissue or skin micro-injury through laser induced optical breakdown (LIOB) or melanin assistant optical breakdown. The subsequent collagen remodeling stimulated by such micro-injury will result in skin rejuvenation. The current microchip laser is capable to generate more than 40 mJ 300 ps laser pulses with wavelength of 1064 nm. Therefore, the output energy from the microchip laser can be split into for example, 10 micro-beams although other numbers of micro-beams are possible. Each micro-beam will have more than 4 mJ which is sufficient for effective skin treatment. Each of the micro-beams could be focused by focusing optics to generate 10 micro-dots.

Skin treatment usually requires irradiation of a two-dimensional skin area. There is a number of approaches to implement two dimensional micro-beam pattern, for example, splitting the microchip laser beam into a one-dimensional array of micro-beams and manually sliding the one-dimensional array of micro-beams over the skin. Another approach is use of scanning system to scan the array of micro-beams in one or two direction/axes. Use of micro-beams or fractional beams with scanning mirrors or other scanning means supports fractional skin treatment.

Figure 6:
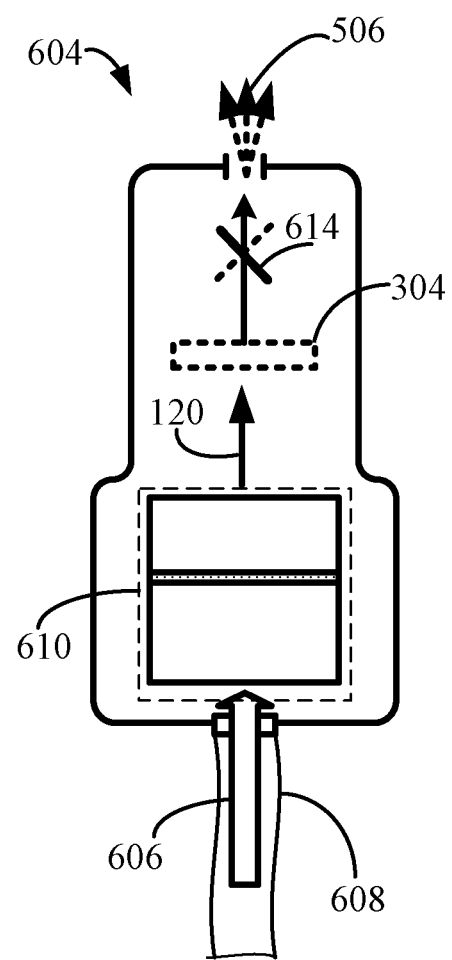
FIG. 6 is an example of a handpiece for fractional skin treatment.

FIG. 6 is an example of a handpiece for fractional skin treatment. For example, the exciting Alexandrite laser could be located in a cabinet and as disclosed in the U.S. Pat. No. 9,722,392 to the same assignee and inventor and incorporated herein in its entirety, the Alexandrite pump laser beam schematically shown by arrow 606 could be conducted by a fiber optics connection to a seed microchip laser 610 located in handpiece body 604 configured to be applied to the skin. Handpiece body 604 could include a high energy seed microchip laser 610 identical to the described above microchip lasers and a unit of scanning mirrors 614 or a polygon spinner or other laser beam scanning means supporting laser beam 120 scanning in one or two directions or axes (X, Y). This would facilitate implementation of fractional skin treatment. The whole system of seed microchip laser 610 and scanning mirrors 614 could be small enough to be packed into handpiece 604. Such handpiece can generate picosecond laser allowing for fractional treatment for skin rejuvenation.

An optional Second or higher Harmonic Generator 304 could be located in handpiece body 604. Microchip laser 610 emits a beam with wavelength of 1064 nm. When additional to 1064 nm wavelength is required, Second Harmonic Generator 304 could be introduced into microchip laser beam path to generate an additional laser light wavelength. Generally, other wavelength frequency multiplying devices could be arranged on a turret and used when required.

Figure 7:
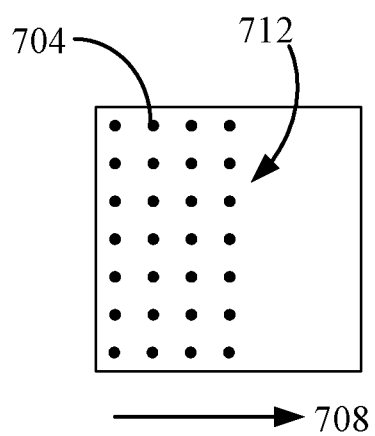
FIG. 7 is an example of a sparse fractional skin treatment pattern.

For skin treatment, as illustrated in FIG. 7, the caregiver or user could manually slide handpiece 604 with one-dimensional (1-D) beam splitter, for example, a holographic 1-D beamsplitter or scanner over the treated skin area forming a fractionated scanning system. In course of the sliding movement, microchip seed laser 610 generates picosecond laser pulses forming a 1-D fractionated micro-dot 704 line.

Figure 8:
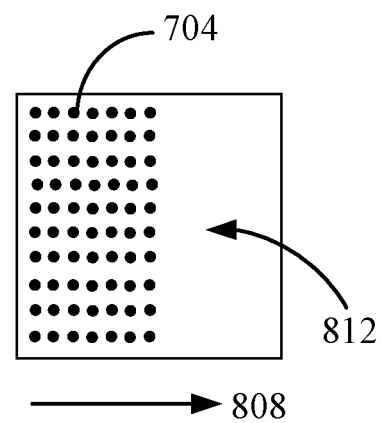
FIG. 8 is an example of a denser fractional skin treatment pattern.

Manual movement of handpiece in a direction perpendicular to 1-D fractionated micro-dot line as shown by arrow 708 generates a 2-D fractional beam pattern 712. The fractional treated skin area coverage can be changed by varying the number of fractionated micro-dot 704 in a 1-D line and movement speed of handpiece 604. FIG. 7 is an example of a relatively sparse located fractionated micro-dot 704 in a 1-D line. Handpiece 604 movement speed 708 is higher than the same handpiece movement speed 808 (FIG. 8). Accordingly, a denser 2-D pattern 812 of fractionated micro-dots 704 is generated.

Figure 9:
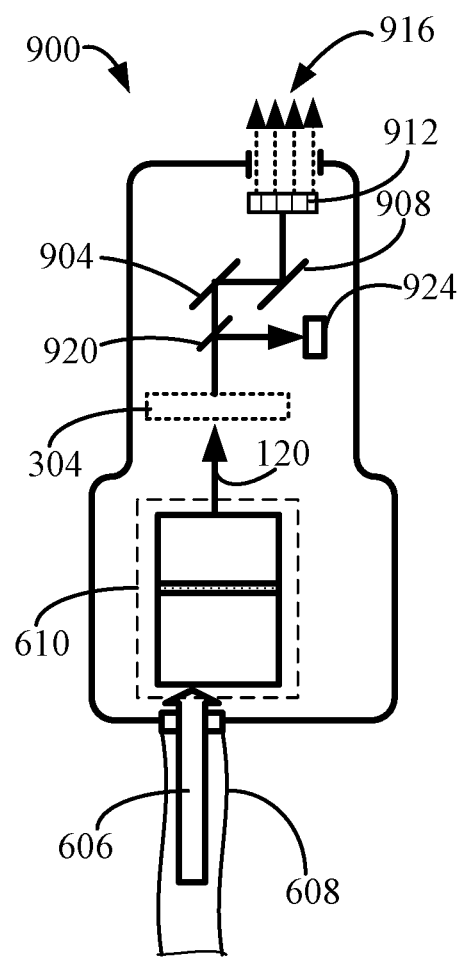
FIG. 9 is another example of a handpiece for fractional skin treatment.

In a further example illustrated in FIG. 9 a handpiece for fractional skin treatment is shown. Generation of a fractionated beam pattern is produced by a combination of a pair of galvanometer mirrors 904 and 908 that project or scan laser beam 120 onto a lens array 912. Lens array 912 splits laser beam 120 into a plurality of microbeams 916 which could also be fractionated microbeams. Mirror 920 could be used to separate additional wavelength generated by Second or higher Harmonic generator 304 could be located in harmonic generators. The coating of mirror 920 is formed accordingly to the desired wavelength separation. The unconverted infrared light 120 could be directed and absorbed in a laser light beam dump 924 while the harmonics could be delivered to the treated skin segment containing a combination of skin disorders. Laser light beam dump 924 could be designed to effectively dissipate the unconverted infrared energy without getting damaged or causing a rise in temperature of other handpiece 900 components. Passive and active cooling mechanisms can be used as need to remove heat from the laser light beam dump 924.

The example below provides some operational parameters of a typical handpiece used for skin disorders treatment. Seed laser 610 energy could be 40 mJ or more. The system is such designed that energy for each microbeam is up to 4 mJ at 1064 nm and 2 mJ at 532 nm.

Such seed laser energy is high enough so that each laser beam from the seed laser can cover at least 9 lenslets to generate 9 micro-dots. Galvanometer mirror pair 904 and 908 scans the laser beam nine times to form a 2-D pattern and cover at least 81 lenslets. Assuming that microchip laser operates at a frequency of 20 Hz, each scan will take 0.45 second (9/20) or the treatment can be operated up to 2.2 Hz.

It will be appreciated by persons skilled in the art that the present disclosure is not limited to what has been particularly shown and described hereinabove. Rather, the scope of the microchip laser and handpiece includes both combinations and sub-combinations of various features described hereinabove as well as modifications and variations thereof which would occur to a person skilled in the art upon reading the foregoing description and which are not in the prior art.

LIST OF REFERENCES (1) X. Guo, et. al, "12 mJ Yb:YAG/Cr:YAG microchip laser", Opt. Lett., 43(3), 459, 2018
(2) L. Zheng, etc, ">MW peak power at 266 nm, low jitter kHz repetition rate from intense pumped microlaser", Opt. Exp., 24(25), 28748, 2016
(3) H. He, et. al, Ming-Ming Zhang, Jun Dongl and Ken-Ichi Ueda, "Linearly polarized pumped passively Q-switched Nd:YVO4 microchip laser for Ince-Gaussian laser modes with controllable orientations", J. Opt., 18(12), 125202 (2016)
(4) V. Vitkin, et. al, "Compact 0.7 mJ/11 ns eye-safe erbium laser" Laser Physics, 26(12), 125801 (2016).
(5) J. Nikkinen, VILLE-MARKUS KORPIJÄRVI, IIRO LEINO, ANTTI HÄRKÖNEN, AND MIRCEA GUINA, "Frequency-doubled passively Q-switched microchip laser producing 225 ps pulses at 671 nm", 41(22), 5385 (2016).
(6) C. Wang, et. al, "1.2 MW peak power, all-solid-state picosecond laser with a microchip laser seed and a high gain single-passing bounce geometry amplifier", Optics & Laser Technology", 85, 14 (2016)
(7) J. Dong, et. al, "A Cr4+:YAG passively Q-switched Nd:YVO4 microchip laser for controllable high-order Hermite-Gaussian modes", Laser Physics, 26, 095004 (2016)
(8) E. Türkyilmaz, et. al, "Simple ps microchip Nd:YVO4 laser with 3.3-ps pulses at 0.2 to 1.4 MHz and single-stage amplification to the microjoule level", Opt. Eng., 55(6), 0661296(2016).
(9) P. Loiko, et. al, "Sub-nanosecond Yb:KLu(WO4)2 microchip laser" Opt. Lett., 41(11), 2620(2016)
(10) A. C. Butler, et. al, "Scaling Q-switched microchip lasers for shortest pulses", Appl. Phys., 109, 81(2012)
(11) M. Tsunekane, et. al, "High Peak Power, Passively Q-switched Microlaser for Ignition of Engines" IEEE J. Quan. Elec., 46(2), 277(2010).
(12) R. Bhandari, et. al, ">6 MW peak power at 532 nm from passively Q-switched Nd:YAG/Cr4+:YAG microchip laser", Optical Express, 19(20), 19135(2011)
(13) P. Peuser, et. al, "Miniaturized, high-power diode-pumped, Q-switched Nd:YAG laser oscillator-amplifier", Appl. Opt., 50(4), 399(2011)
(14) N. Pavel, et. al, "Composite, all-ceramics, high-peak power Nd:YAG/Cr4+:YAG monolithic micro-laser with multiple-beam output for engine ignition" Opt. Express, 19(10), 9378(2011)
(15) R. Haring, et. al, "Passively Q-switched microchip laser at 1.5 mm", J. Opt. Soc. Am. B., 18(12), 1805(2001)
(16) A. STRATAN, L. RUSEN*, R. DABU, C. FENIC, C. BLANARU "Picosecond laser system based on microchip oscillator", J. Opto. Adv. Mat., 10(11), 3022(2008).
(17) A. H. Curtis, et. al, "Demonstration of a compact 100 Hz, 0.1 J diode-pumped picosecond laser" Opt. Lett., 36(11), 2164(2011)
(18) A. Agnesi, et. al, "50-mJ macro-pulses at 1064 nm from a diode-pumped picosecond laser system" Opt. Exp., 19(21), 20316(2011)
(19) G. Salamu, et. al, "High Peak Power, Passively QSwitched, Composite, All Poly Crystalline Ceramics Nd:YAG/Cr4+:YAG Laser and Generation of 532 nm Green Light" Solid State and Liquid Lasers, 22(1), 68(2012)
(20) Q. K. Aia, et. al, "Picosecond Nd:YLF FivePasses Laser Amplifier with 20 mJ Pulse Energy", Solid State and Liquid Lasers, 22(7), 1169(2012)
(21) J. Zayhowski, "Q-switched operation of microchip lasers", 16(8), 575(1991)
(22) W. Kong, "Diode edge-pumped passively Q-switched microchip laser", Opt. Eng., 54(9), 090501(2015)
(23) C. Y. Cho, et. Al., "An energy adjustable linearly polarized passively Q-switched bulk laser with a wedged diffusion bonded Nd:YAG/Cr4+:YAG crystal", Optical Express, 23(6), 8162(2015)
(24) J. Dong, et. al ">1 MW peak power, an efficient Yb:YAG/Cr4:YAG composite crystal passively Q-switched laser", Laser Physics, 24, 55801(2014).
(25) A. Agnesi, et. al, "Low-power 100-ps microchip laser amplified by a two-stage Nd:YVO4 amplifier module", Appl. Phys. B 109, 659(2012)
(26) R. Bhandari, et. al, "3 MW peak power at 266 nm using Nd:YAG/Cr4+:YAG microchip laser and fluxless-BBO", Optical Material Express, 2(7), 907(2012)
(27) A. Steinmetz, "Sub-5-ps, multimegawatt peak-power pulse from a fiber-amplified and optically compressed passively Q-switched microchip laser", Opt. Lett., 37(13), 2550(2012).

(28) O. Sandu, et. al, "High-peak power, passively Q-switched, composite, all-polycrystalline ceramic Nd:YAG/Cr4+:YAG lasers, Quan. Elec., 42(3), 211(2012)

(29) R. Bhandari, et. al, ">6 MW peak power at 532 nm from passively Q-switched Nd:YAG/Cr4+:YAG microchip laser", Opt. Exp., 19(20), 19135(2011)

What is claimed is:

1. A microchip laser comprising;
a laser medium with input and output facets,
an input facet coated with a highly reflective dielectric coating at microchip laser wavelength and highly transmissive at pump wavelength,
an output facet coated with a highly reflective at pump wavelength dielectric coating;
and highly transmissive at Q-switched laser wavelength, and
a saturable absorber attached by intermolecular forces to output facet of microchip laser and output facet coated by a dielectric coating partially reflective at microchip laser wavelength.

2. The microchip laser of claim 1, wherein a coating of output facet considers refractive indices of laser medium and saturable absorber such that coating functions as required when a monolithic material is formed.

3. The microchip laser of claim 1, wherein laser medium material and saturable absorber are made of the same host material.

4. The microchip laser of claim 1, wherein laser medium material and saturable absorber are made of different host materials.

5. The microchip laser according to claim 1 wherein bonding between laser medium and saturable absorber is implemented through optical contact by intermolecular forces.

6. The microchip laser of claim 1 wherein the microchip laser is a double pass pumped microchip laser.

7. The microchip laser according to claim 1 wherein a double pass pumped microchip laser supports pump laser absorption and shorter medium length leading to shorter pulse duration as well as a more compact laser layout.

8. The microchip laser of claim 1 wherein the highly reflective dielectric coating at an interface between laser medium and saturable absorber at pump wavelength supports achieving double passing pumping and avoids unwanted bleaching of passive Q-switch by unabsorbed pump laser.

9. A laser system, comprising:
a pump laser configured to provide a pumping laser beam;
a handpiece including:
a microchip laser configured to receive the pumping laser beam, the microchip laser includes a cavity formed by a gain medium and saturable absorber; and
a passive Q-switched element activated by a laser beam emitted by the microchip laser;
wherein the laser system generates ultrashort high power laser pulses.

10. The laser system according to claim 9 wherein the microchip laser is a double pass pumped microchip laser.

11. The laser system according to claim 10 wherein the double pass pumped microchip laser supports sufficient pump laser absorption and shorter medium length leading to shorter pulse and a more compact laser layout.

12. The laser system according to claim 9, wherein a highly reflective dielectric coating film of the microchip laser supports achieving double passing pumping and avoids unwanted bleaching of passive Q-switch by unabsorbed pump laser.

13. The laser system according to claim 9, wherein bonding between laser medium and saturable absorber is implemented through optical contact by intermolecular forces.

14. The laser system according to claim 9, wherein gain medium and saturable absorber are made of the same host material.

15. The laser system according to claim 9 wherein gain medium and saturable absorber are made of different host material.

16. The laser system according to claim 9 wherein the pump laser is an Alexandrite laser.

* * * * *